United States Patent [19]

Kleeman et al.

[11] Patent Number: 5,374,604

[45] Date of Patent: Dec. 20, 1994

[54] HERBICIDAL 2,6-SUBSTITUTED PYRIDINES

[75] Inventors: Axel Kleeman, Hanau, Germany; David Munro, Maidstone; Bipin Patel, Sittingbourne, both of United Kingdom

[73] Assignee: American Cyanamid Company, Wayne, N.J.

[21] Appl. No.: 67,655

[22] Filed: May 26, 1993

[30] Foreign Application Priority Data

May 27, 1992 [EP] European Pat. Off. ............ 92304795

[51] Int. Cl.$^5$ ................. C07D 213/69; A01N 43/40
[52] U.S. Cl. ..................... 504/130; 546/296
[58] Field of Search ................ 504/130; 546/296

[56] References Cited

U.S. PATENT DOCUMENTS

| | | | |
|---|---|---|---|
| 3,535,328 | 10/1970 | Zielinski | 546/275 |
| 3,687,959 | 8/1972 | Zielinski | 546/291 |
| 4,235,621 | 11/1980 | Nishiyama et al. | |
| 4,830,846 | 5/1989 | Jackson, Jr. et al. | 423/488 |

FOREIGN PATENT DOCUMENTS

| | | | |
|---|---|---|---|
| 0021613 | 1/1981 | European Pat. Off. | |
| 0180188 | 5/1986 | European Pat. Off. | |
| 0535980 | 4/1993 | European Pat. Off. | 546/296 |
| 1527714 | 6/1968 | France | 546/296 |
| 2923371 | 12/1979 | Germany | |
| 59-031-758-A | 2/1984 | Japan | |
| 59-031-761-A | 2/1984 | Japan | |
| 63-250-324-A | 10/1988 | Japan | |

OTHER PUBLICATIONS

Holmes, J. of Biological Chemistry, vol. 247, No. 23, pp. 7628-7633, Dec. 10, 1972.
Mertes et al. J. of Med. Chem, vol. 10, No. 2, pp. 320-325, 1962.

*Primary Examiner*—C. Warren Ivy
*Assistant Examiner*—Zinna N. Davis
*Attorney, Agent, or Firm*—Michael P. Morris

[57] ABSTRACT

A herbicidal composition which comprises at least one carrier and, as active ingredient, a compound of the general formula

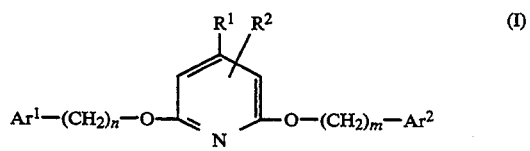

in which each of n and m independently is 0 or 1; each of $Ar^1$ and $Ar^2$ independently is an aryl group, at least one of $Ar^1$ and $Ar^2$ being substituted by one or more of the same or different substituents selected from halogen atoms, alkyl groups, alkoxy groups, haloalkyl groups and haloalkoxy groups; and $R^1$ is hydrogen, or an alkyl, alkylthio or haloalkyl group having from 1 to 4 carbon atoms, and $R^2$ is hydrogen or a halogen atom provided that at least one of $R^1$ and $R^2$ represents a hydrogen atom. Certain compounds of formula I are novel.

9 Claims, No Drawings

HERBICIDAL 2,6-SUBSTITUTED PYRIDINES

BACKGROUND OF THE INVENTION

The present invention is concerned with certain 2,6-substituted pyridines, their preparation and use as herbicides.

Pyridines and pyridine derivatives have many uses, for example, as pharmaceuticals, pesticides (herbicides, acaricides, anthelmintics, and bird repellants), feed supplements, solvents, reagents, intermediates, and chemicals for the polymer and textile industry. Various 2,6-diaryloxy- or -diarylmethoxy-pyridine derivatives have been investigated for such uses, the compounds often having additional substitution of the central pyridine ring.

European Patent A2-180188 is concerned with 2-hydroxy-pyridine derivatives, for example 2,6-dihydroxypyridines, as potentiators for increasing the anticancer activity of 5-fluorouracil and related compounds. The preparation and debenzylation of 2,6-dibenzyloxy-3-chloropyridine is disclosed. In J. Biol. Chem., 72, Vol. 247(23), pages 7628 to 7633, (which is concerned with the synthesis of 2,3,6-trihydroxypyridine and accumulation and partial characteristics of the product of 2,6-dihydroxypyridine oxidation) the Grignard reaction of 3-bromo-2,6-dibenzyloxypyridine with isopropyl bromide is disclosed. There is no disclosure of biological activity for 2,6-dibenzyloxy-3-chloropyridine nor its bromo analogue.

2,6-di(3-methylphenoxy)-pyridine is disclosed in French Patent Specification No. 1527714 which is concerned with polyethers containing a 2,6-linked pyridine group. U.S. Pat. No. 4,830,846 is concerned with a separation process for anhydrous HCl and HBr by thermal cleavage utilizing a hindered pyridine, one example of which being 2,6-diphenoxypyridine. Again no biological activity is disclosed for these aryloxy pyridines.

The dibenzyloxy analogue of 2,6-diphenoxypyridine in addition to being mentioned in JP-A-63250324, EP-A-180188 and J. Med. Chem. 10(2), pages 320 to 325, all medical research publications, was prepared as an example of the herbicidal compounds proposed in U.S. Pat. No. 3,535,328 and the divisional published as U.S. Pat. No. 3,687,959. Both texts are predominantly directed to the herbicidal, fungicidal, and, for the compounds claimed in U.S. Pat. No. 3,535,328, nematocidal and insecticidal activity, of amido or aminothioethoxy derivatives. No herbicidal activity data is given for the disclosed 2,6-dibenzyloxypyridine.

Herbicidal evaluation of 2,6-dibenzyloxypyridine and its analogue 2,6-diphenoxypyridine now undertaken has revealed that the compounds have herbicidal activity primarily against representative broadleaf plant species in post-emergence foliar spray application but little or no post-emergence action against representative grass-type plants and a complete absence of pre-emergence herbicidal activity.

Surprisingly, it has now been found that certain substituted forms of 2,6-diphenoxypyridine and 2,6-dibenzloxypyridine, and also the related asymmetric 2-phenoxy-6-dibenzyloxy-pyridines, have a significantly different spectrum of activity and not only possess high activity against broadleaf plants in foliar spray applications but also have significant action against grass-type plants, particularly against the important weed, barnyard grass; a number of examples additionally being effective against both plant types pre-emergence.

Accordingly, the present invention provides a herbicidal composition which comprises a carrier and, as an active ingredient, a compound of the general formula

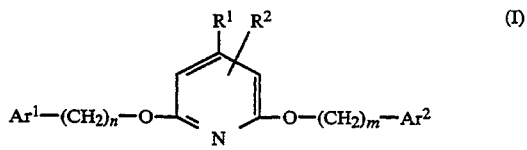

in which each of n and m independently is 0 or 1; each of Ar¹ and Ar² independently is aryl, at least one of Ar¹ and Ar² being substituted by one or more of the substituents selected from halogen, alkyl, alkoxy, haloalkyl and haloalkoxy; and R¹ is a hydrogen atom, or alkyl, alkylthio or haloalkyl having from 1 to 4 carbon atoms, and R² is hydrogen or halogen provided that at least one of R¹ and R² is hydrogen.

An alkyl group, unless otherwise specified may be a straight chain or branched chain group suitably containing up to 12 carbon atoms, preferably from 1 to 4 carbon atoms. An alkyl portion of a haloalkyl, alkylthio, alkoxy or haloalkoxy group suitably has from 1 to 4 atoms, preferably 1 or 2 carbon atoms.

Halogen is fluorine, chlorine, bromine or iodine. Haloalkyl and haloalkoxy are preferably mono-, di- or trifluoroalkyl and -alkoxy, especially trifluoromethyl and trifluoromethoxy.

An aryl group is preferably a phenyl group.

The Ar¹—(CH₂)ₙ—O— and Ar²—(CH₂)ₘ—O— portions of compounds of formula I are identical or different. Thus the compounds are symmetrical or asymmetrical diaryloxypyridines or diarylmethoxy-pyridines, or are aryloxyarylmethoxypyridines.

Preferably one of n and m is 1 and the other is 0 or 1, but most preferably each of n and m is 1.

At least one of the groups Ar¹ and Ar² is substituted. Suitable substituents include methoxy and trifluoromethoxy groups and, preferably, methyl, flourine, chlorine, or trifluoromethyl. From 1 to 5 substituents are present; preferably 1 or 2 substituents.

R¹ is preferably a hydrogen atom or a methyl, methylthio or trifluoromethyl group. Especially preferred is hydrogen or methyl.

R² is suitably a hydrogen or chlorine atom, especially a hydrogen atom.

Preferred compounds fall in the following categories, with reference to the symbols used in general formula I:

(i) n is 0; m is 0; R¹ and R² each represents a hydrogen atom; Ar¹ represents a trifluoromethylphenyl group, especially a 3-trifluoromethylphenyl group; and Ar² represents an unsubstituted or chloro- or trifluoromethyl-substituted phenyl group;

(ii) n is 0; m is 1; R¹ and R² each represents a hydrogen atom; Ar¹ represents a substituted phenyl group, especially a 3-trifluoromethylphenyl group; and Ar² represents an unsubstituted phenyl group or a fluoro-substituted phenyl group;

(iii) n is 1; m is 1; R¹ and R² each represents a hydrogen atom; and each of Ar¹ and Ar² represents a fluoro- or methyl- substituted phenyl group, especially ortho and/or para substituted, e.g., 2- or 4-fluorophenyl group or a 2-methyl group.

Most of the compounds of general formula I are novel and accordingly the present invention provides a compound of general formula I in which n, m, $Ar^1$, $Ar^2$, $R^1$ and $R^2$ have the meanings given above with the proviso that a) when n and m are 0, then both $Ar^1$ and $Ar^2$ are not 3-methylphenyl; and
b) when n and m are both 1, then $R^2$ does not represent a chlorine or bromine atom.

The compounds of formula I may be prepared by appropriate adaptation of conventional methods of obtaining substituted pyridine compounds, the basic technique being, for example, reaction of a metal salt of the appropriate alcohol with an appropriate 2,6-dihalopyridine, in a solvent and suitably at elevated temperature, ideally at reflux. For symmetrical pyridine compounds preparation, the reaction can be carried out in one step by using a molar ratio of salt to pyridine of at least 2:1. For asymmetrical compounds of formula I, separate introduction of the two substituents is required in a two-stage process.

The present invention therefore provides a process for the preparation of a compound of formula I, which comprises a) to obtain a compound of formula I in which $Ar^1$ and $Ar^2$ are the same, reacting a metal salt of a compound of general formula

$$Ar^1(CH_2)_nOH \qquad (II)$$

in which $Ar^1$ and n are as defined above, with a 2,6-halopyridine of the formula

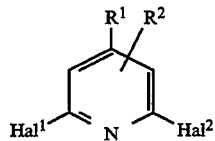

(III)

in which $Hal^1$ and $Hal^2$ each, independently, represent a halogen atom, and $R^1$ and $R^2$ are as defined above, in a molar ratio of at least 2:1 or b) to obtain a compound of formula I in which $Ar^1$ and $Ar^2$ are different, reacting a compound of formula II with a 2,6-dihalopyridine of formula III in a molar ratio of 1:1 and then reacting the resulting product with a metal salt of a compound of the formula IV

$$Ar^2(CH_2)_nOH \qquad (IV)$$

in which $Ar^2$ and n are as defined in claim 1, in a molar ratio of at least 1:1, each reaction stage being carried out in the presence of an organic solvent.

The metal salt of the alcohol of formula II is conveniently an alkali metal salt, for example a sodium or potassium salt, and is conveniently generated by reaction of the alcohol with a suitable metal base, for example a metal carbonate or hydride. Preferably the metal salt is a sodium salt generated using sodium hydride.

The organic solvent utilized in the reaction would be selected depending on the nature of the reactants involved. Generally any polar organic solvent is suitable, for example dimethylformamide and tetrahydrofuran.

$Hal^1$ and $Hal^2$ conveniently are both the same, each representing a chlorine or bromine atom.

The prepared compounds of formula I may, if desired, be isolated and purified using conventional techniques.

Compounds of general formula II, III and IV are generally known and/or are easily preparable by standard techniques.

The present invention also provides the use of a compound of formula I as a herbicide. Further, in accordance with the invention there is provided a method of combating undesired plant growth at a locus by treating the locus with a composition according to the invention or a compound of formula I. As the most useful action is by foliar spray application, the locus is most suitably the plants in a crop area, typical crops being cereals. However, application may also be to the soil for those compounds having pre-emergence herbicidal action. The dosage of active ingredient used is in the range of from about 0.01 kg/ha to about 10 kg/ha, preferably about 0.1 kg/ha to about 1.0 kg/ha.

While all compounds of the present invention have useful activity against broadleaf and narrowleaf plants, exceptionally good activity is shown by compounds in which at least one of n and m is 1, particularly in the phenoxy/benzyloxy pyridines and, most preferably, in the dibenzyloxypyridines of the present invention.

The present invention also extends to a method of making a herbicidal composition of the invention which comprises bringing a compound of formula I into association with at least one carrier.

Preferably, there are at least two carriers in a composition of the present invention, at least one of which carriers is a surface-active agent.

A carrier in a composition according to the invention is any material with which the active ingredient is formulated to facilitate application to the locus to be treated, which may be, as appropriate, a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain about 0.5% to about 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilizers, for example superphosphates.

Suitable liquid carriers include water; alcohols, for example ispropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which carriers is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The herbicidal composition of the invention may also contain other active ingredients, for example compounds possession insecticidal or fungicidal properties, or other herbicides.

The following Examples illustrate the invention. The structures of the compounds prepared in the following Examples were additionally confirmed by mass spectrometry and NMR.

PREPAATION OF 2,6-DIARYLOXYPYRIDINES

EXAMPLE 1

Preparation of 2,6-di-[3-trifluoromethoxyphenoxy]pyridine

3-Trifluoromethoxyphenol (19 g; 0.106 mol) was added to oil-free sodium hydride (2.7 g) in dry dimethylformamide (120 ml). 2,6-Dichloropyridine (8 g; 0.054 mol) was then added and the reaction mixture refluxed for 4 hours. The symmetrical phenoxy pyridine 2,6-di-[3-trifluoromethoxyphenoxy]-pyridine was isolated, following conventional work up, chromatography and distillation procedures, as a colorless oil (17 g; yield 73%). Boiling point: 145° C. at 3 mm Hg.

EXAMPLE 2

Preparation of 2,6-di-(3-trifluoromethylphenoxy)-4-methylthiopyridine

To a solution of 2,6-dichloro-4-nitropyridine (3.8 g; 0.02 mol) in dimethylformamide (50 ml) cooled with an ice-bath was sodium thiomethoxide (1.4 g; 0.02 mol) slowly added. After stirring for 3 hours, the reaction mixture was quenched with water (300 ml) and extracted 3 times each with a hexane/ethyl acetate mixture (100 ml; 1/1). The combined extracts were dried with anhydrous magnesium sulphate and the solvent was removed in vacuo. Purification by silica gel flash column chromatography afforded 2,6-dichloro-4-methylthiopyridine (2.9 g; 74%) as a colorless oil.

A mixture of 2,6-dichloro-4-methylthiopyridine (0.97 g; 0.005 mol), 3-hydroxybenzotrifluoride (1.3 ml; 10.4 mmol) and sodium hydride (0.2 g) was reacted and worked up according to the procedure of Example 1 above to give 2,6-di-(3-trifluoromethyl phenoxy)-4-methylthiopyridine (1.9 g; 85%)

EXAMPLE 3

Preparation of 2,6-di-(3-trifluoromethylphenoxy)-4-methylpyridine

To a solution of 2-methyl-2-chloromethyloxirane (50 g; 0.47 mol) in concentrated hydrochloric acid (23 ml) at ice-bath temperature was added a solution of sodium cyanide (27.4 g; 0.56 mol) in hydrochloric acid (23 ml). After stirring for 10 hours at that temperature, the reaction mixture was warmed to 40° C. and a solution of potassium cyanide (33.8 g; 0.52 mol) in water (50 ml) was added. The reaction mixture was warmed to 50° C. and stirred for 4 hours. After cooling, the mixture was neutralized and extracted 3 times each with ethyl acetate (150 ml). The combined extracts were dried with anhydrous magnesium sulphate. Removal of the solvent in vacuo afforded 1,3-dicyano-2-methyl-2-hydroxypropane (56.4 g; 96%). This compound was added carefully to a 33% wet solution of hydrogen bromide in glacial acetic acid at ice-bath temperature. The reaction mixture was stirred for 3 days at ambient temperature. The solvent was removed in vacuo and the residual oil brought to pH 12 with a 10 molar aqueous solution of sodium hydroxide. The alkaline solution was extracted 3 times each with ethyl acetate (100 ml). The extracts were combined and the solvent removed in vacuo to afford 6-amino-2-bromo-4-methylpyridine (56 g; 66%) as colorless crystals. Melting point 99° C.

A solution of 6-amino-2-bromo-4-methylpyridine (45.2 g, 0.24 mol) in water (100 ml) and concentrated sulphuric acid (43 g) at 0° C. was stirred and a solution of sodium nitrite (13.2 g; 0.19 mol) in water (20 ml) was added. After 2 hours, the reaction mixture was warmed to 60° C. and stirred for 1 hour. After cooling, the mixture was extracted with dichloromethane (200 ml). The solvent was removed in vacuo to afford 2-bromo-4-methyl-6-hydroxypyridine (20.2 g; 56%) as colorless crystals. Melting point 152° C. This material was mixed with tribromomethane (100 ml) and phosphoryl bromide (24 g) and heated to reflux for 3 hours. After cooling, the reaction mixture was quenched carefully with an aqueous 50% solution of sodiumhydroxide and the mixture extracted twice each with dichloromethane (100 ml). The solvent was removed in vacuo and the crude product purified by flash silica gel column chromatography using hexane/ethyl acetate (7/3). 2,6-Dibromo-4-methylpyridine (6.9 g; 25%) was obtained. Melting point 77° C. This compound (1.3 g; 5.2 mmol) was then converted using 3-hydroxybenzotrifluoride (1.4 ml; 10.7 mmol) and sodium hydride according to the procedure of Example 1 above to give 2,6-di-(3-trifluoromethylphenoxy)-4-methylpyridine as an oil (1.8 g; 84%).

EXAMPLE 4

Preparation of 2-(3-trifluoromethylphenoxy)-6-(4-fluorophenoxy)-pyridine a) Preparation of 2-(3-trifluoromethylphenoxy)-6-chloropyridine 3-trifluoromethylphenol (65 g; 0.40 mol) was added dropwise and with stirring to a suspension of oil-free sodium hydride (10 g) in dry dimethylformamide (250 ml) maintained under a nitrogen atmosphere. After 30 minutes 2,6-dichloropyridine (59.5 g; 0.40 mol) was added and the reaction mixture refluxed with stirring for 1½ hours.

Dimethylformamide was removed in vacuo, and solvent extraction carried out using a chloroform/water mixture (1l; 50/50). Following purification and then chromatography, a colorless oil (88 g; 80%) was obtained from the organic extraction layer, and identified as 2-(3-trifluoromethylphenoxy)-6-chloropyridine.

Boiling point: 120° C. at 2 mm Hg.

b) Preparation of 2-(3-trifluoromethylphenoxy)-6-(4-fluorophenoxy)pyridine

The procedure of a) above was followed using 4-fluorophenol (8 g; 0.07 mol) in dry dimethylformamide (20 ml), sodium hydride (2 g) also in dry dimethylformamide (60 ml), 2-(3-trifluoromethylphenoxy)-6-chloropyridine from a) above (19.5 g; 0.07 mol) with a 2 hour reflux. The asymmetrical phenoxypyridine 2-(3-trifluoromethylphenoxy)-6-(4-fluorophenoxy)pyridine (18.9 g; 76%) was derived as a colorless oil from the organic layer of chloroform/water (500 ml; 50/50) following solvent extraction.

Boiling point: 145° C. at 1 mm Hg

PREPARATION OF ARYLOXY-ARYLMETHOXY-PYRIDINES

EXAMPLE 5

Preparation of 2-(3-trifluoromethylphenoxy)-6-benzyloxypyridine a) Preparation of 2-benzyloxy-6-chloropyridine Following the procedure of Example 4a) above, benzyl alcohol (5 g; 46 mmols) reacted with sodium hydride (1.19 g), was refluxed for 1 hour with 2,6-dichloropyridine (6.9 g; 46 mmols) using sodium hydride and dry dimethylformamide as solvent. 2-Benzyloxy-6-chloropyridine (6.1 g; 60%) was obtained as a colorless oil following solvent extraction with chloroform/water (500 ml; 50/50), purification and chromatographic separation of the product from the organic layer, identified by elemental analysis and mass spectrum.

b) Preparation of 2-(3-trifluoromethylphenoxy)-6-benzyloxypyridine

The procedure of Example 4a) was also used to introduce the 3-trifluoromethyl phenoxy group by reaction of 2-benzyloxy-6-chloropyridine (5 g; 23 mmols) from a) above with 3-trifluoromethylphenol (3.3 g; 0.018 mols) using dry sodium hydride (0.55 g) and dry dimethylformamide (200 ml) as solvent, with a 1 hour reflux stage. 2-(3-Trifluoromethylphenoxy)-6-benzyloxypyridine (4.9 g; 51%) was obtained as a yellow oil following solvent extraction (chloroform/water—500 ml; 50/50), and chromatography plus distillation of the organic layer.

Boiling point: 145° C. at 2 mm Hg.

PREPARATION OF 2,6-DIARYLMETHOXYPYRIDINES

EXAMPLE B

Preparation of 2,6-dibenzyloxypyridine

Benzyl alcohol (5.1 g; 0.05 mols) was reacted with 2,6-dichloropyridine (3.5 g; 0.024 mols) utilizing sodium hydride (1.2 g) and, as solvent, dimethylformamide by the procedure of Example 1 above. Usual work up, chromatography and recrystallisation gave 2,6-dibenzyloxypyridine as a colorless solid (5.5 g; 81%). Melting point: 74° C.

EXAMPLES NOS. 6 to 25

Compounds according to the invention were prepared following the relevant preparation technique of the above Examples 1 to 5 and B and using appropriate starting materials.

Details of Examples 6 to 25 are given in Table 1 below, identification being by reference to the substituents shown in the following formula:

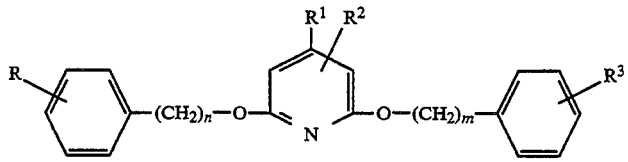

In Table 1 'bp' indicates boiling point and 'mp' indicates melting point. Elemental analysis data is given in Table 1a following.

TABLE 1

| Ex. No. | R | n | $R^1$ | $R^2$ | m | $R^3$ | Identification Data |
|---|---|---|---|---|---|---|---|
| 6 | 3-$CF_3$ | 0 | H | H | 0 | 3-$CF_3$ | bp 150° C./1 mmHg |
| 7 | 3-$OCF_3$ | 0 | H | H | 0 | H | bp 150° C./1 mmHg |
| 8 | 3-$CF_3$ | 0 | H | H | 0 | 2-F | bp 165° C./2 mmHg |
| 9 | 3-$CF_3$ | 0 | H | H | 0 | 3-F | bp 180° C./2 mmHg |
| 10 | 3-$CF_3$ | 0 | H | H | 0 | 2,4-$F_2$ | bp 150° C./1 mmHg |
| 11 | 3-$CF_3$ | 0 | H | H | 0 | 3-$CH_3$ | bp 160° C./2 mmHg |
| 12 | 3-$CF_3$ | 0 | H | H | 0 | 3-Cl | bp 160° C./2 mmHg |
| 13 | 3-$CF_3$ | 0 | H | H | 0 | 4-Cl | bp 150° C./3 mmHg |
| 14 | 3-$CF_3$ | 0 | H | Cl | 0 | 3-$CF_3$ | bp 175° C./2 mmHg |
| 15 | 3-$CF_3$ | 0 | H | H | 0 | 3-$OCH_3$ | — |
| 16 | 3-$CF_3$ | 0 | H | H | 0 | 4-$CH_3$ | — |
| 17 | 3-$CF_3$ | 0 | $CF_3$ | H | 0 | 3-$CF_3$ | bp 160° C./2 mmHg |
| 18 | 3-$CF_3$ | 0 | H | H | 1 | 3-F | bp 135° C./3 mmHg |
| 19 | 2-$CH_3$ | 1 | H | H | 1 | 2-$CH_3$ | bp 165° C./3 mmHg |
| 20 | 3-Cl | 1 | H | H | 1 | 3-Cl | bp 180° C./2 mmHg |
| 21 | 4-Cl | 1 | H | H | 1 | 4-Cl | mp 51-52° C. |

TABLE 1-continued

| Ex. No. | R | n | R¹ | R² | m | R³ | Identification Data |
|---|---|---|---|---|---|---|---|
| 22 | 2-F | 1 | H | H | 1 | 2-F | bp 170° C./ 3 mmHg |
| 23 | 3-F | 1 | H | H | 1 | 3-F | bp 180° C./ 2 mmHg |
| 24 | 4-F | 1 | H | H | 1 | 4-F | mp 82-84° C. |
| 25 | 3-CF₃ | 1 | H | H | 1 | 3-CF₃ | bp 155° C./ 2 mmHg |

TABLE 1A

| Example No. | Elemental Analysis (%) | | | | | |
|---|---|---|---|---|---|---|
| | Calculated | | | Found | | |
| | C | H | N | C | H | N |
| 1 | 52.9 | 2.5 | 3.3 | 53.6 | 3.0 | 3.6 |
| 2 | 53.9 | 2.9 | 3.1 | 53.7 | 2.7 | 3.1 |
| 3 | 58.1 | 3.2 | 3.4 | 57.9 | 3.1 | 3.4 |
| 4 | 61.9 | 3.2 | 4.0 | 62.1 | 3.2 | 4.4 |
| 5 | 66.1 | 4.1 | 4.1 | 66.3 | 5.0 | 4.5 |
| 6 | 57.1 | 2.8 | 3.5 | 56.6 | 3.1 | 3.8 |
| 7 | 65.3 | 3.6 | 4.2 | 65.7 | 3.1 | 3.5 |
| 9 | 61.9 | 3.2 | 4.0 | 62.3 | 3.7 | 3.9 |
| 10 | 58.9 | 2.7 | 3.8 | 58.6 | 2.9 | 4.3 |
| 11 | 66.1 | 4.1 | 4.3 | 66.3 | 4.3 | 4.2 |
| 12 | 59.1 | 3.0 | 3.8 | 60.1 | 3.0 | 3.5 |
| 13 | 59.1 | 3.0 | 3.8 | 59.3 | 3.5 | 4.1 |
| 14 | 52.6 | 2.3 | 3.2 | 54.6 | 3.1 | 4.0 |
| 15 | 63.2 | 3.9 | 3.9 | 63.0 | 3.8 | 4.0 |
| 16 | 66.1 | 4.1 | 4.1 | 65.9 | 4.0 | 3.8 |
| 17 | 51.4 | 2.1 | 3.0 | 51.2 | 2.1 | 3.2 |
| 18 | 61.4 | 3.3 | 4.2 | 61.0 | 3.4 | 4.4 |
| 19 | 79.0 | 6.6 | 4.4 | 78.7 | 6.3 | 4.3 |
| 21 | 63.3 | 4.2 | 3.9 | 63.7 | 4.3 | 3.8 |
| 22 | 69.7 | 4.6 | 4.3 | 69.5 | 3.9 | 3.9 |
| 23 | 69.7 | 4.5 | 4.3 | 70.9 | 5.0 | 3.5 |
| 24 | 69.7 | 4.6 | 4.3 | 69.6 | 4.6 | 5.0 |
| 25 | 59.0 | 3.5 | 3.3 | 60.2 | 3.7 | 3.3 |

EXAMPLE 26

Herbicidal Activity

To evaluate their herbicidal activity, compounds were tested using, as a representative range of monocotyledon plants: maize, Zea mays (Mz); rice, Oryza sativa (R); barnyard grass, Echinochloa crus-galli (BG); and oat, Avena sativa (O). As a representative range of dicotyledon plants, the following were also used: linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a test compound, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 liters per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence tests untreated soil bearing seedling plants were used as controls.

The herbicidal effects of the test compounds were assessed visually twelve days after spraying the foliage and the soil, and thirteen days after drenching the soil, and were recorded on a 0-9 scale. A rating 0 indicates growth as untreated control, a rating 9 indicates death. An increase of 1 unit on the linear scale approximates to a 10% increase in the level of effect.

The results of the tests are set out in Table 2 below. In the Table, a blank space indicates a rating 0; an asterisk indicates that no result was obtained.

Compound B is the compound 2,6-dibenzyloxypyridine, melting point 74° C., disclosed as the compound of Example No. 81 of Table I(b) of U.S. Pat. No. 3,535,328 and its divisional U.S. Pat. No. 3,687,959. Compound A is the corresponding diphenoxy compound, 2,6-diphenoxypyridine, boiling point 170° C. at 5 mmHg. The herbicidal activity of these compounds was assessed by the procedure given above, and the results included in Table 2: the data for compound A precedes that for the diphenoxy compounds 1 to 16 of the present invention and the data for compound B precedes that for the dibenzyloxy compounds 19 to 25 of the present invention.

TABLE 2

| Example No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| A | | | | | | | | | 5 | 3 | 2 | 2 | 3 | 5 | 9 | 6 | 2 | | | | | | | | |
| | | | | | | | | | 1 | 1 | | 1 | 1 | 3 | 7 | 2 | 1 | | | | | | | | |
| 1 | | | 1 | 2 | 1 | 3 | 2 | | 5 | 4 | 1 | 5 | 5 | 4 | 8 | 9 | 6 | 1 | | 3 | | | 5 | 1 | |
| | | | | | | | | | 1 | 3 | | 1 | 2 | 2 | 8 | 8 | 3 | | | 1 | | | 2 | | |
| 2 | | | 5 | 2 | | 6 | | | 5 | 6 | | 8 | 6 | 6 | 8 | 9 | 7 | | | 8 | 4 | 1 | 8 | 7 | |
| | | | | | | | | | 1 | 4 | | 8 | 5 | 4 | 8 | 8 | 6 | | | 7 | | | 7 | 6 | |
| 4 | | | 3 | 1 | 1 | | | | 5 | 5 | 2 | 7 | 5 | 4 | 9 | 8 | 6 | 3 | 1 | 6 | 3 | 2 | 5 | 3 | |
| | | | | | | | | | 1 | 3 | | 3 | 2 | 3 | 8 | 8 | 3 | 1 | | 2 | 1 | | 3 | | |
| 5 | 6 | 4 | 7 | 5 | 3 | 7 | 7 | 3 | 5 | 5 | 5 | 8 | 6 | 7 | 9 | 9 | 7 | 5 | 1 | 8 | 5 | 3 | 8 | 6 | |
| | | | | | | | | | 1 | 2 | 1 | 4 | 3 | 5 | 9 | 8 | 4 | 1 | | 6 | 1 | 1 | 5 | 3 | |
| 6 | 2 | 1 | 4 | 3 | 2 | 4 | 3 | 1 | 5 | 5 | 3 | 6 | 5 | 5 | 9 | 9 | 6 | 4 | 3 | 7 | 5 | 4 | 8 | 7 | 1 |
| | | | | | | | | | 1 | 2 | 1 | 4 | 4 | 4 | 9 | 9 | 4 | 2 | 1 | 5 | 1 | | 6 | 4 | |
| 7 | 2 | 1 | 2 | 1 | | | | | 5 | 6 | 2 | 6 | 4 | 5 | 8 | 8 | 5 | 1 | | 6 | 4 | 2 | 4 | 2 | |
| | | | | | | | | | 1 | 4 | | 2 | 2 | 4 | 8 | 8 | 4 | | | 3 | | | 2 | | |
| 8 | | | | | | | | | 5 | 6 | 4 | 8 | 6 | 7 | 9 | 9 | 7 | | | 4 | 3 | | 7 | 3 | 2 |
| | | | | | | | | | 1 | 3 | | 3 | 3 | 6 | 9 | 8 | 6 | | | | | | 2 | | |
| 9 | | | | | | | | | 5 | 5 | 4 | 8 | 8 | 8 | 9 | 9 | 8 | | | | | | | | |
| | | | | | | | | | 1 | 3 | 2 | 6 | 4 | 7 | 9 | 9 | 7 | | | | | | | | |

TABLE 2-continued

| Example No. | Soil drench 10 kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 10 | | | 1 | 1 | 1 | | | | 5 | 6 | 2 | 7 | 4 | 5 | 9 | 9 | 6 | 1 | | 4 | 1 | | 6 | 2 | |
| | | | | | | | | | 1 | 4 | | 2 | 2 | 2 | 9 | 8 | 5 | 1 | | 1 | | | 2 | | |
| 11 | | | | | | | | | 5 | 5 | 2 | 7 | 5 | 7 | 9 | 9 | 5 | | 1 | 4 | 2 | | 4 | 3 | |
| | | | | | | | | | 1 | 3 | | 4 | 3 | 6 | 9 | 9 | 4 | | | | | | 4 | 1 | |
| 12 | | | | | | | | | 5 | 7 | 5 | 8 | 7 | 8 | 9 | 9 | 7 | 2 | 2 | 7 | 6 | 2 | 8 | 7 | 3 |
| | | | | | | | | | 1 | 5 | 2 | 6 | 5 | 7 | 9 | 9 | 7 | 1 | | 5 | 4 | | 6 | 3 | 1 |
| 13 | | | 3 | 3 | 4 | 3 | 1 | | 5 | 5 | 4 | 6 | 6 | 7 | 9 | 9 | 6 | | 2 | 6 | 4 | 2 | 7 | 6 | |
| | | | | | | | | | 1 | 3 | 3 | 3 | 4 | 6 | 9 | 8 | 5 | | | | | | 6 | | |
| 14 | | | | | | | | | 5 | 6 | 2 | 5 | 5 | 4 | 9 | 9 | 6 | 1 | | 5 | | | 4 | | |
| | | | | | | | | | 1 | 3 | | 1 | 2 | 2 | 8 | 7 | 4 | | | | | | 2 | | |
| 15 | | | | | | | | | 5 | 5 | | 7 | 4 | 5 | 9 | 9 | 7 | 1 | | 5 | | | 1 | | |
| | | | | | | | | | 1 | 2 | | 5 | 3 | 4 | 8 | 9 | 6 | | | | | | | | |
| 16 | | | | | | | | | 5 | 5 | 2 | 7 | 3 | 6 | 9 | 9 | 6 | | | | | | | | |
| | | | | | | | | | 1 | 3 | | 2 | | 2 | 6 | 3 | 5 | | | | | | | | |
| 17 | | | | | | | | | 5 | 5 | | 6 | 3 | 6 | 7 | 6 | 6 | | | 5 | | | 1 | | |
| | | | | | | | | | 1 | | | | 2 | 1 | | | 2 | | | 2 | | | | | |
| 18 | 2 | 2 | 5 | 5 | 3 | 3 | 1 | | 5 | 6 | 5 | 8 | 7 | 8 | 9 | 9 | 7 | | | | | | * | * | |
| | | | | | | | | | 1 | 4 | 3 | 6 | 6 | 9 | 8 | 6 | | | | | | | 4 | 2 | |
| B | | | | | 5 | | | | 5 | 3 | | 4 | 2 | 4 | 9 | 8 | 4 | | | | | | | | |
| | | | | | | | | | 1 | 1 | | 2 | | 3 | 9 | 7 | 4 | | | | | | | | |
| 19 | | | | | | | | | 5 | 4 | 5 | 8 | 5 | 7 | 9 | 9 | 5 | 2 | | 8 | 4 | | 7 | 4 | |
| | | | | | | | | | 1 | 2 | 1 | 6 | 3 | 6 | 8 | 9 | 3 | | | 2 | | | 3 | | |
| 20 | | | | | | | | | 5 | 6 | | 6 | 4 | 6 | 9 | 9 | 5 | | | | | | | | |
| | | | | | | | | | 1 | 3 | | 2 | 2 | 3 | 8 | 7 | 3 | | | | | | | | |
| 21 | | | | | | | | | 5 | 5 | | 7 | 4 | 6 | 8 | 9 | 6 | | | | | | 2 | | |
| | | | | | | | | | 1 | 3 | | 5 | 2 | 5 | 8 | 7 | 5 | | | | | | | | |
| 22 | 4 | 2 | 5 | 5 | | | | | 5 | 4 | 6 | 8 | 6 | 7 | 9 | 9 | 6 | 3 | 2 | 8 | 6 | 3 | 8 | 8 | |
| | | | | | | | | | 1 | 2 | 2 | 7 | 5 | 6 | 9 | 8 | 5 | | | 6 | 3 | | 7 | 5 | |
| 23 | | | | | | | | | 5 | 7 | 2 | 8 | 4 | 6 | 9 | 9 | 7 | | | 6 | | | 1 | | |
| | | | | | | | | | 1 | 4 | | 6 | 1 | 4 | 9 | 8 | 5 | | | | | | | | |
| 24 | | | | 1 | 1 | 3 | | | 5 | 4 | 2 | 9 | 4 | 6 | 9 | 9 | 5 | | | 3 | | | 1 | 2 | |
| | | | | | | | | | 1 | 2 | | 8 | 2 | 6 | 9 | 8 | 5 | | | | | | | | |
| 25 | | | | | | | | | 5 | 5 | | 5 | 4 | 5 | 9 | 7 | 6 | | | | | | | | |
| | | | | | | | | | 1 | 2 | | 2 | 1 | 3 | 7 | 5 | 4 | | | | | | | | |

What is claimed is:

1. A herbicidal composition which comprises a carrier and, as active ingredient, an effective amount of a compound of the formula

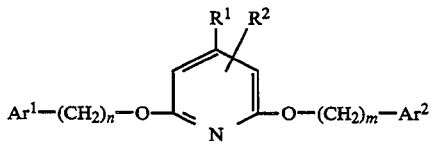

(I)

in which each of n and m independently is 0 or 1; each of $Ar^1$ and $Ar^2$ independently is aryl, at least one of $Ar^1$ and $Ar^2$ being substituted by one or more of the substituents selected from halogen atoms, alkyl groups, alkoxy groups, haloalkyl groups and haloalkoxy groups; and $R^1$ is a hydrogen atom, or an alkyl, alkylthio or haloalkyl group having from 1 to 4 carbon atoms, and $R^2$ is hydrogen or halogen provided that at least one of $R^1$ and $R^2$ represents a hydrogen atom.

2. The composition of claim 1, in which at least one of n and m is 1.

3. The composition of claim 2, in which each of n and m is 1.

4. The composition of claim 1 in which the substituents of $Ar^1$ and $Ar^2$ are independently selected from methyl groups, methoxy groups, fluorine atoms, chlorine atoms, trifluoromethyl and trifluoromethoxy groups.

5. The composition of claim 4, in which $R^1$ represents hydrogen and $R^2$ represents hydrogen or chlorine atom, or $R^1$ represents a trifluoromethyl, methylthio or methyl group and $R^2$ represents a hydrogen atom.

6. The composition of claim 1 in which the carrier comprises a surface-active agent.

7. The composition of claim 1 wherein the compound includes the proviso that (a) when n and m are both 0, then both $Ar^1$ and $Ar^2$ are not a 3-methylphenyl group; or (b) when n and m are both 1, then, $R^2$ does not represent a chlorine or bromine atom.

8. A method of combating undesired plant growth at a locus which comprises treating the locus with a composition of claim 1.

9. The method of combating undesired plant growth at a locus which comprises treating the locus with a composition of claim 6.

* * * * *

UNITED STATES PATENT AND TRADEMARK OFFICE
CERTIFICATE OF CORRECTION

PATENT NO.   : 5,374,604
DATED        : December 20, 1994
INVENTOR(S)  : Axel Kleeman It is certified that error appears in the above-identified patent and that said Letters Patent is hereby corrected as shown below:

Title page, item [73], Assignee: should read --SHELL RESEARCH LIMITED --

Signed and Sealed this

Eighteenth Day of July, 2000

Attest:

Q. TODD DICKINSON

*Attesting Officer*            *Director of Patents and Trademarks*